US011079376B1

(12) United States Patent
Najar

(10) Patent No.: US 11,079,376 B1
(45) Date of Patent: Aug. 3, 2021

(54) OPTICAL ANALYTE DETECTOR

(71) Applicant: UNITED ARAB EMIRATES UNIVERSITY, Al Ain (AE)

(72) Inventor: Adel Najar, Al Ain (AE)

(73) Assignee: UNITED ARAB EMIRATES UNIVERSITY, Al Ain (AE)

( * ) Notice: Subject to any disclaimer, the term of this patent is extended or adjusted under 35 U.S.C. 154(b) by 0 days.

(21) Appl. No.: 17/096,747

(22) Filed: Nov. 12, 2020

(51) Int. Cl.
| | |
|---|---|
| *G01J 3/42* | (2006.01) |
| *G01N 33/543* | (2006.01) |
| *G02B 6/12* | (2006.01) |
| *G01N 33/569* | (2006.01) |
| *G01N 21/25* | (2006.01) |
| *G02B 6/293* | (2006.01) |

(52) U.S. Cl.
CPC ....... *G01N 33/54373* (2013.01); *G01N 21/25* (2013.01); *G01N 33/56983* (2013.01); *G02B 6/12004* (2013.01); *G02B 6/12007* (2013.01); *G01N 2201/06113* (2013.01); *G01N 2201/08* (2013.01); *G02B 6/29338* (2013.01); *G02B 2006/12038* (2013.01); *G02B 2006/12121* (2013.01); *G02B 2006/12123* (2013.01); *G02B 2006/12138* (2013.01)

(58) Field of Classification Search
CPC ........ G01J 3/02; G01J 3/42; G01J 3/28; G01J 2003/2866; G01N 21/274
USPC ......................................................... 356/319
See application file for complete search history.

(56) References Cited

U.S. PATENT DOCUMENTS

| | | |
|---|---|---|
| 6,721,053 B1 | 4/2004 | Maseeh |
| 9,097,648 B2 | 8/2015 | Heidrich et al. |
| 9,864,144 B2 | 1/2018 | Schreuder et al. |
| 2004/0023396 A1 | 2/2004 | Boyd et al. |

(Continued)

FOREIGN PATENT DOCUMENTS

WO 2014080358 A2 5/2014

OTHER PUBLICATIONS

Samusenko et al., "A SiON Microring Resonator-Based Platform for Biosensing at 850 nm," Journal of Lightwave Technology, vol. 34, No. 3 Feb. 1, 2016, pp. 969-977.

(Continued)

*Primary Examiner* — Md M Rahman
(74) *Attorney, Agent, or Firm* — Nath, Goldberg & Meyer; Richard C. Litman

(57) ABSTRACT

The optical analyte detector is a photonic detector that uses a measured wavelength shift to determine the presence of an analyte. An open cell is formed in an optical layer for receiving a sample to be analyzed. A transition metal dichalcogenide monolayer defines a bottom wall of the open cell, and the transition metal dichalcogenide monolayer is formed directly above a microring resonator. A waveguide is positioned adjacent to the open cell, and is spaced apart therefrom by a gap. The waveguide is coupled to the microring resonator, and the transition metal dichalcogenide monolayer is functionalized with an adsorbed layer for detection of a specific analyte. Molecular binding takes place if a sample of the analyte contacts the adsorbed layer, which induces a wavelength shift in light transmitted through the waveguide. The presence of this measured wavelength shift indicates positive detection of the analyte.

16 Claims, 2 Drawing Sheets

(56) References Cited

U.S. PATENT DOCUMENTS

| | | | | |
|---|---|---|---|---|
| 2012/0156802 A1* | 6/2012 | Flagan | ............... | H01S 5/0622 |
| | | | | 436/501 |
| 2013/0261010 A1* | 10/2013 | Bailey | ............... | G01N 27/72 |
| | | | | 506/9 |
| 2013/0295688 A1* | 11/2013 | Bailey | ............ | G01N 33/54373 |
| | | | | 436/501 |
| 2020/0069225 A1 | 3/2020 | Vizbaras et al. | | |

OTHER PUBLICATIONS

Besselink et al., "Performance of Arrayed Microring Resonator Sensors with the TriPleX Platform," Journal of Biosensors & Bioelectronics, 7.2, 2016.

Shiue et al., "Active 2D materials for on-chip nanophotonics and quantum optics," Nanophotonics, vol. 6, Issue 6, Mar. 15, 2017, pp. 1329-1342.

Koo et al., "Arch-shaped multiple-target sensing for rapid diagnosis and identification of emerging infectious pathogens," Biosensors and Bioelectronics, 119, 2018, pp. 79-85.

Palestino et al., "Can nanotechnology help in the fight against COVID-19?," Expert review of anti-infective therapy, 2020, pp. 1-16.

Zhang et al., "Recent advances in the detection of respiratory virus infection in humans," Journal of medical virology, 92.4, 2020, pp. 408-417.

Chin et al., "Design and Modeling of Waveguide-Coupled Single-Mode Microring Resonators", IEEE Journal of Lightwave Technology (1998), vol. 16, No. 8, pp. 1433-1446.

Bogaerts e al., "Silicon microring resonators", Laser Photonics Rev. (2012), ol. 6, No. 1, pp. 47-73.

Asghari et al., "Fast Accurate Point of Care COVID-19 Pandemic Diagnosis Enabled Through Advanced Lab-on-a-Chip Optical Biosensors: Opportunities and Challenges", arXiv.2008.08572 [physics-ins-det] (2020), 52 pages.

Soler et al., "How Nanophototonic Label-Free Biosensors Can Contribute to Rapid and Massive Diagnostics of Respiratory Virus Infections: COVID-19 Case", ACS Sensors (2020), https://dx.doi.org/10.1021/acssensors.0c01180, 16 pages.

Soler et al., "Engineering phototonics solutions for COVID-19", APL Phototonics (2020), vol. 5 090901, https://doi.org/10.1063/5.0021270, 14 pages.

* cited by examiner

OPTICAL ANALYTE DETECTOR

BACKGROUND

1. Field

The disclosure of the present patent application relates to silicon (or silicon carbide) photonic biosensor devices, and particularly to an optical analyte detector that uses a measured wavelength shift to determine presence of the analyte.

2. Description of the Related Art

Photonic devices have been used to detect the presence of various analytes, such as viruses in test samples. Silicon photonic devices, in particular, have been used in a variety of different configurations for the testing of viral infection, including waveguide sensors, microring resonator-based sensors, and Mach-Zehnder interferometer-based sensors. A number of common photonic sensors are based on optical ring resonators using silicon-on-insulator (SOI) technology. A ring resonator is composed of a silicon-based waveguide on top of a buried oxide substrate. In general, the light of a tunable laser is coupled to the waveguide via a grating coupler or by butt coupling. The light is then partly coupled to the ring resonator, and if the resonance condition is fulfilled, resonance peaks can be found in the output spectrum. At the output, the light is coupled to a photodetector or an optical spectrum analyzer, depending on the light source.

Currently, lasers, photodiodes and photonic sensors can be monolithically integrated on the same chip. After the fabrication of the chip, the surface of the silicon ring resonator is functionalized with an adsorbed layer for specific detection. Molecular binding takes place if a sample of the analyte contacts the adsorbed layer on top of the silicon waveguide. This will induce a resonance wavelength shift, proving detection. However, the general sensing mechanism underlying the operation of such sensors is evanescent field sensing, which is not only less than 100% accurate, but which can be influenced by a wide variety of differing ambient environmental factors. Since such detectors are often used for the detection of viruses and other serious infections, such potential inaccuracies can be potentially deadly. Thus, an optical analyte detector solving the aforementioned problems is desired.

SUMMARY

The optical analyte detector is a detector for an analyte in a sample. The optical analyte detector includes a light source, such as a laser, for generating a first optical signal having a first wavelength, a substrate, and an optical layer formed on the substrate. First and second open cells are formed in an upper surface of the optical layer. First, second, and third waveguides are each embedded in the optical layer, with the second and third waveguides optically coupled to the first waveguide by a first optical splitter, such that the first optical signal is transmitted from the first waveguide into the second and third waveguides with equal power transmission. The second waveguide is positioned adjacent to the first open cell and the third waveguide is positioned adjacent to the second open cell. Additionally, a fourth waveguide is also embedded in the optical layer and directly optically couples the light source to the first waveguide. A primary microring resonator is embedded in the optical layer, adjacent the fourth waveguide, such that the primary microring resonator is optically coupled to the fourth waveguide.

A first transition metal dichalcogenide monolayer is embedded in the optical layer and defines a bottom wall of the first open cell and, similarly, a second transition metal dichalcogenide monolayer is also embedded in the optical layer and defines a bottom wall of the second open cell. A first microring resonator is embedded in the optical layer beneath the first transition metal dichalcogenide monolayer and is coupled thereto, the first microring resonator being positioned adjacent to the second waveguide and separated therefrom by a first gap. Similarly, a second microring resonator is embedded in the optical layer beneath the second transition metal dichalcogenide monolayer and is coupled thereto, the second microring resonator being positioned adjacent to the third waveguide and separated therefrom by a second gap.

A first photodetector receives a second optical signal having a second wavelength from the second waveguide, and a second photodetector receives a third optical signal having a third wavelength from the second waveguide. A first comparator is in communication with the first and second photodetectors for comparing the second and third wavelengths and calculating a first wavelength shift therebetween. The first open cell is adapted to be a reference cell and the second open cell is adapted to receive a first sample to be analyzed for the presence of an analyte. The first comparator determines the presence of the analyte when the first wavelength shift is within a preset range.

These and other features of the present subject matter will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
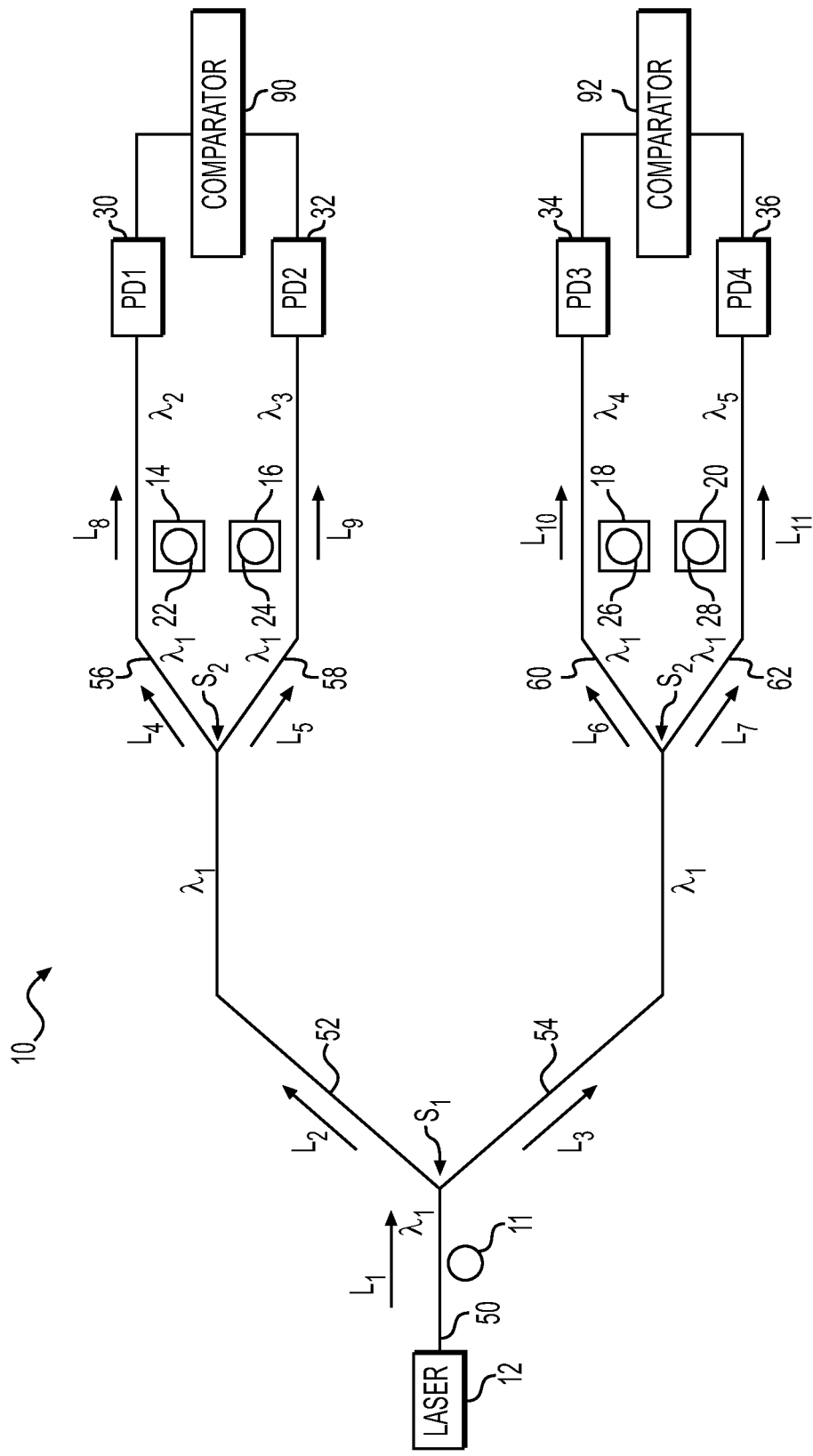
FIG. 1 is a schematic diagram of an optical analyte detector.
Figure 2:
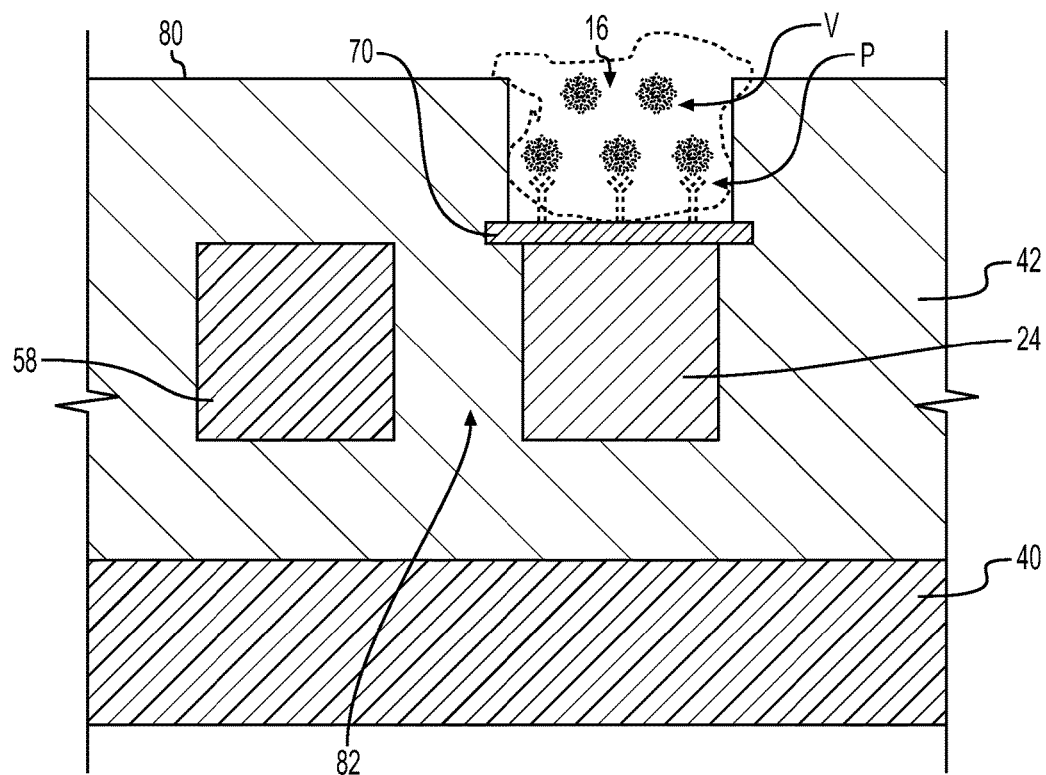
FIG. 2 is a partial side view in section of the optical analyte detector of FIG. 1.

The optical analyte detector 10 is a detector for an analyte in a sample. As shown in FIGS. 1 and 2, the optical analyte detector 10 includes a light source, such as a laser 12, for generating a first optical signal with a first wavelength $\lambda_1$, a substrate 40, and an optical layer 42 formed on the substrate 40. FIG. 1 illustrates a configuration of the optical analyte detector 10 where two samples may be analyzed at once.

Optical signal $L_1$ is split into two optical signals $L_2$, $L_3$ (with equal power splitting) by an optical splitter $S_1$, and analysis may be performed simultaneously on two separate samples in the upper branch (following optical signal $L_2$ in FIG. 1) and the lower branch (following optical signal $L_3$ in FIG. 1), respectively. For purposes of explanation and simplification, analysis in the upper branch of FIG. 1 will be explained first in what follows, followed by a description of analysis in the lower branch (which operates in an identical manner to the upper branch). It should be understood that any suitable numbers of branches may be used, so that any suitable number of analyses may take place simultaneously, and that the two branches illustrated in FIG. 1 are shown for exemplary purposes only. The optical analyte detector 10 is a silicon photonic biosensor. It should be understood that the term "silicon photonic biosensor", as used herein, is not limited to pure silicon devices, but includes any silicon-based photonic biosensor material, including silicon, silicon oxide(s), carbides, salts, and compounds and combinations thereof, as known in the art.

It should be understood that the substrate 40 and optical layer 42 may be formed from any suitable material. For example, substrate 40 may be formed from silicon or silicon carbide, and optical layer 42 may be formed from silicon dioxide. Similarly, it should be understood that light source need not be a laser 12, but may be any suitable type of light source. For example, the laser 12 may be a III-V vertical cavity surface emitting laser (VCSEL) laser.

Referring now to the upper branch in FIG. 1, first and second open cells 14, 16, respectively, are formed in an upper surface 80 of the optical layer 42. First, second, and third waveguides 52, 56, 58, respectively, are each embedded in the optical layer 42. The second and third waveguides 56, 58 are optically coupled to the first waveguide 52 by first optical splitter $S_2$, such that the first optical signal (with first wavelength $\lambda_1$) is transmitted from the first waveguide 52 into the second and third waveguides 56, 58 with equal power transmission. Thus, optical signal $L_2$ is split into optical signals $L_4$ and $L_5$, each having equal power and each still having a wavelength of $\lambda_1$. The second waveguide 56 is positioned adjacent to the first open cell 14 and the third waveguide 58 is positioned adjacent to the second open cell 16. It should be understood that any suitable type of optical junctions or splitters may be used. Additionally, a fourth waveguide 50 is also embedded in the optical layer and directly optically couples the light source 12 to the first waveguide 52. A primary microring resonator 11 is embedded in the optical layer 42 adjacent the fourth waveguide 50, such that the primary microring resonator 11 is optically coupled to the fourth waveguide 50. For the above exemplary materials, first, second, third and fourth waveguides 52, 56, 58, 50, respectively, may each be a silicon or silicon carbide waveguide.

FIG. 2 illustrates the second open cell 16. However, it should be understood that each open cell and the structures associated therewith are manufactured in a similar manner. As shown in FIG. 2, a second transition metal dichalcogenide monolayer 70 is embedded in the optical layer 42 and defines a bottom wall of the second open cell 16. The first open cell 14 is manufactured in an identical manner, and a first transition metal dichalcogenide monolayer is similarly embedded in the optical layer 42 and defines a bottom wall of the first open cell 14. A second microring resonator 24 is embedded in the optical layer 42, beneath the second transition metal dichalcogenide monolayer 70 and is coupled thereto. The second microring resonator 24 is positioned adjacent to the third waveguide 58 and separated therefrom by a second gap 82. Similarly, a first microring resonator 22 is embedded in the optical layer 42 beneath the first transition metal dichalcogenide monolayer and is coupled thereto. The first microring resonator 22 is positioned adjacent to the second waveguide 56 and separated therefrom by a first gap.

It should be understood that each of the first and second transition metal dichalcogenide monolayers may be formed from any suitable type of transition metal dichalcogenide. Representative examples of transition metal dichalcogenides include $MoS_2$, $MoSe_2$, $WS_2$, and $WSe_2$. Further, it should be understood that each of the first and second transition metal dichalcogenide monolayers may be formed using any suitable method. As an example, each layer may be prepared by mechanical exfoliation and transferred onto the top of the corresponding microring resonator. It should be further understood that the relative dimensions of the first and second open cells 14, 16 are illustrated for exemplary purposes only. For example, each of the first and second open cells 14, 16 may have a surface area on the order of a few $mm^2$. The particular dimensions of the first and second open cells, the first and second gaps, and the first and second microring resonators may be selected such that, in combination with their respective waveguides, a monomode waveguide is formed.

A first photodetector (PD1) 30 receives a second optical signal $L_8$ from the second waveguide 56, having a second wavelength $\lambda_2$, and a second photodetector (PD2) 32 receives a third optical signal $L_9$ from the second waveguide 58, having a third wavelength $\lambda_3$. The photodetectors 30, 32 may be photodiodes. A first comparator 90 is in communication with the first and second photodetectors 30, 32, respectively, for comparing the second and third wavelengths $\lambda_2$, $\lambda_3$, respectively, and calculating a first wavelength shift therebetween. It should be understood that the first comparator 90 may be any suitable type of comparator, such as a comparator circuit, a microprocessor, a computer, a programmable logic controller or the like. The first open cell 14 is adapted to be a reference cell and the second open cell 16 is adapted to receive a first sample to be analyzed for the presence of an analyte. The first comparator 90 determines the presence of the analyte when the first wavelength shift is within a preset range.

Returning to FIG. 1, the lower branch operates in an identical manner, such that a second sample may be analyzed simultaneously with the first sample. In the lower branch of FIG. 1, third and fourth open cells 18, 20, respectively, are also formed in the upper surface of the optical layer 42. Fifth, sixth and seventh waveguides 54, 60, 62, respectively, are embedded in the optical layer 42, where the first waveguide 52 and the fifth waveguide 54 are optically coupled to the fourth waveguide 50 by a second optical splitter $S_1$. The fourth waveguide 50 is directly coupled to the light source 12, such that optical signal $L_1$ is split into optical signals $L_2$ and $L_3$, each with the first wavelength $\lambda_1$. As discussed above, a primary microring resonator 11 is embedded in the optical layer 42, adjacent the fourth waveguide 50, such that the primary microring resonator 11 is optically coupled to the fourth waveguide 50. The sixth waveguide 60 and the seventh waveguide 62 are optically coupled to the fifth waveguide 54 by a third optical splitter $S_3$, such that the optical signal $L_3$ is split into optical signals $L_6$ and $L_7$, each having equal power. The sixth waveguide 60 is positioned adjacent to the third open cell 18 and the seventh waveguide 62 is positioned adjacent to the fourth open cell 20.

Similar to the upper branch, a third transition metal dichalcogenide monolayer is embedded in the optical layer 42 and defines a bottom wall of the third open cell 18. Similarly, a fourth transition metal dichalcogenide monolayer is embedded in the optical layer 42 and defines a bottom wall of the fourth open cell 20. A third microring resonator 26 is embedded in the optical layer 42 beneath the third transition metal dichalcogenide monolayer and is coupled thereto. The third microring resonator 26 is positioned adjacent to the sixth waveguide 60 and separated therefrom by a third gap. Similarly, a fourth microring resonator 28 is embedded in the optical layer 42 beneath the fourth transition metal dichalcogenide monolayer and is coupled thereto. The fourth microring resonator 28 is positioned adjacent to the seventh waveguide 62 and separated therefrom by a fourth gap.

A third photodetector (PD3) 34 receives a fourth optical signal $L_{10}$ from the sixth waveguide 60, which has a fourth wavelength $\lambda_4$. Similarly, a fourth photodetector (PD4) 36 receives a fifth optical signal $L_{11}$ from the seventh waveguide 62, which has a fifth wavelength $\lambda_5$. A second comparator 92, similar to the first comparator 90, is in communication with the third and fourth photodetectors 34, 36, respectively, for comparing the fourth and fifth wavelengths $\lambda_4$, $\lambda_5$, respectively, and calculating a second wavelength shift therebetween. Similar to the upper branch, the third open cell 18 is adapted to be a reference cell and the fourth open cell 20 is adapted to receive a second sample to be analyzed for the presence of the analyte. The second comparator 92 determines the presence of the analyte when the second wavelength shift is within the preset range.

In the example shown in FIG. 2, the second open cell 16 receives a nasopharyngeal swab suspended in a universal transport medium (UTM). In the particular example of FIG. 2, the swab is infected with the SARS-CoV-2 virus V, and the open cell 16 has at least one antibody selectively binding to the SARS-CoV-2 spike protein P already received therein (in the UTM), specific to detection of SARS-CoV-2 virus V. In this example, reference cell 14 would only have the UTM with the SARS-CoV-2 spike protein antibody P suspended therein (i.e., without the additional swab sample from a patient). The SARS-CoV-2 spike protein antibody P may be adsorbed on the surface of the transition metal dichalcogenide monolayer.

Specific to the above example for rapid COVID-19 detection, in order to enhance the detection of the virus, the SARS-CoV-2 spike antibody P solution may be prepared using 1-pyrenebutyric acid N-hydroxysuccinimide ester (PBASE) as a probe linker. The SARS-CoV-2 spike antibody P is used as a COVID-19 virus detection platform in this example, since it is essential for specific binding with the SARS-CoV-2 antigen. A specific volume of SARS-CoV-2 spike protein antibody P is suspended in the UTM and is deposited in both the sample cell 16 and the reference cell 14.

The measurement of the wavelength shift ($\Delta\lambda$) represents the difference between the wavelengths transmitted through the reference arm (e.g., $\lambda_2$ of waveguide 56) and the detection arm (e.g., $\lambda_3$ of waveguide 58). If $\Delta\lambda$ is less than 0.01 nm, then the patient is determined to not be infected with COVID-19, and if $\Delta\lambda$ is greater than 0.01 nm, then the patient is determined to be infected with COVID-19.

Figure 3A:
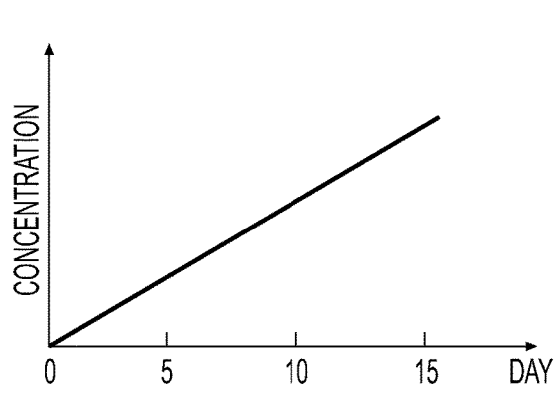
FIG. 3A is a graph showing a calibration curve for calibrating the optical analyte detector, showing COVID-19 concentration as a function of days of exposure as determined by PCR (polymerase chain reaction).

In order to calibrate the optical analyte detector 10, in the example of detecting COVID-19 in a patient, polymerase chain reaction (PCR) may be used to measure the concentration of SARS-CoV-2 virus for patients in the same age range after 5 days, 10 days, and 15 days. FIG. 3A illustrates an exemplary plot of SARS-CoV-2 virus concentration as a function of days after exposure for such PCR testing.

Figure 3B:
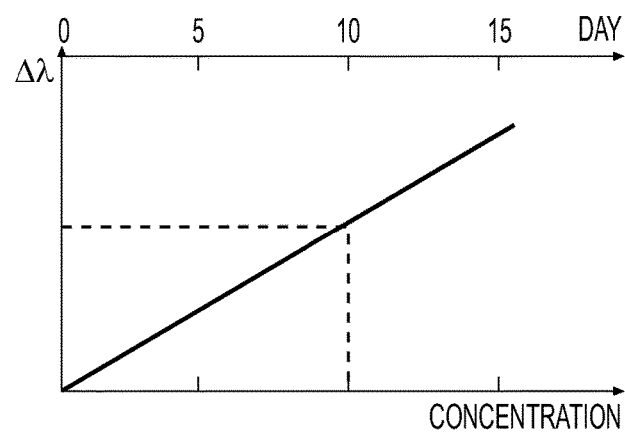
FIG. 3B is a graph showing an output wavelength shift measured by the optical analyte detector for a viral analyte as a function of days of exposure combined with a plot of COVID-19 concentration as a function of days of exposure as determined by PCR, showing results for viral concentration as a function of day after infection by measurement of the wavelength shift, representing a reference chart to determine the approximate COVID-19 concentration and infection day by the measurement of the wavelength shift for a patient with the same general age and health conditions.

For the same group of patients, optical analyte detector 10 may then be used to measure the variation of $\Delta\lambda$ as a function of days (5, 10 and 15 days in this example) after exposure, as shown in FIG. 3B, along with the corresponding measured SARS-CoV-2 virus concentration for each day. By measuring $\Delta\lambda$ for the patient and using the graph of FIG. 3B, information about the stage of contamination (i.e., the number of days after contamination) and the day of contamination can be extracted. FIG. 3B represents a reference chart to determine the approximate COVID-19 concentration and infection day by the measurement of the wavelength shift for a patient with the same general age and health conditions It is to be understood that the optical analyte detector is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. An optical analyte detector, comprising:
a light source for generating a first optical signal having a first wavelength;
a substrate;
an optical layer formed on the substrate, the optical layer having an upper surface;
first and second open cells defined in the upper surface of the optical layer, the first open cell being adapted for receiving a reference sample and the second open cell being adapted for receiving a test sample to be analyzed for presence of the analyte;
a first waveguide embedded in the optical layer, the light source transmitting the first optical signal into the first waveguide;
second, third and fourth waveguides embedded in the optical layer, the fourth waveguide directly optically coupling the light source to the first waveguide;
a primary microring resonator embedded in the optical layer adjacent the fourth waveguide, the primary microring resonator being optically coupled to the fourth waveguide;
a first optical splitter disposed between the first waveguide and the second and third waveguides, the first optical splitter splitting the first optical signal between the second and third waveguides into waves of equal power transmission, defining second and third optical signals, respectively;
a first transition metal dichalcogenide monolayer embedded in the optical layer, the first transition metal dichalcogenide monolayer defining a bottom wall of the first open cell;
a second transition metal dichalcogenide monolayer embedded in the optical layer, the second transition metal dichalcogenide monolayer defining a bottom wall of the second open cell;
a first microring resonator embedded in the optical layer beneath the first transition metal dichalcogenide monolayer and coupled thereto, the second waveguide being positioned to optically couple with the first microring resonator;
a second microring resonator embedded in the optical layer beneath the second transition metal dichalcogenide monolayer and coupled thereto, the third waveguide being positioned to optically couple with the second microring resonator;

a first photodetector receiving the second optical signal from the second waveguide, the second waveguide, the first open cell, the first microring resonator, and the first photodetector defining a reference branch;

a second photodetector receiving the third optical signal from the third waveguide, the third waveguide, the second open cell, the second microring resonator, and the second photodetector defining a test branch; and a first comparator in communication with the first and second photodetectors for comparing wavelengths of the optical signals in the reference branch and the test branch and calculating a first wavelength shift therebetween, the detector confirming presence of the analyte in the test sample when the first wavelength shift is greater than 0.01 nm.

2. The optical analyte detector as recited in claim 1, wherein the substrate comprises a silicon or silicon carbide layer.

3. The optical analyte detector as recited in claim 1, wherein the optical layer comprises a silicon dioxide layer.

4. The optical analyte detector as recited in claim 1, wherein the first, second and third waveguides each comprise silicon or silicon carbide.

5. The optical analyte detector as recited in claim 1, wherein each of the first and second transition metal dichalcogenide monolayers comprises a transition metal dichalcogenide selected from the group consisting of $MoS_2$, $MoSe_2$, $WS_2$, and $WSe_2$.

6. The optical analyte detector as recited in claim 1, wherein each of the first and second transition metal dichalcogenide monolayers is functionalized with an adsorbed layer for detection of a particular analyte.

7. The optical analyte detector as recited in claim 1, further comprising:

third and fourth open cells defined in the upper surface of the optical layer, the third open cell being adapted for receiving a second reference sample and the fourth open cell being adapted for receiving a second test sample to be analyzed for presence of the analyte;

fifth, sixth and seventh waveguides embedded in the optical layer;

a second optical splitter disposed between the fourth waveguide and the first and fifth waveguides, the second optical splitter splitting the first optical signal between the first and fifth waveguides into waves of equal power transmission;

a third optical splitter disposed between the fifth waveguide and the sixth and seventh waveguides, the third optical splitter splitting the first optical signal between the sixth and seventh waveguides into waves of equal power transmission, defining fourth and fifth optical signals, respectively;

a third transition metal dichalcogenide monolayer embedded in the optical layer, the third transition metal dichalcogenide monolayer defining a bottom wall of the third open cell;

a fourth transition metal dichalcogenide monolayer embedded in the optical layer, the fourth transition metal dichalcogenide monolayer defining a bottom wall of the fourth open cell;

a third microring resonator embedded in the optical layer beneath the third transition metal dichalcogenide monolayer and coupled thereto, the sixth waveguide being positioned to optically couple with the third microring resonator;

a fourth microring resonator embedded in the optical layer beneath the fourth transition metal dichalcogenide monolayer and coupled thereto, the seventh waveguide being positioned to optically couple with the fourth microring resonator;

a third photodetector receiving the fourth optical signal from the sixth waveguide, the sixth waveguide, the third open cell, the third microring resonator, and the third photodetector defining a second reference branch;

a fourth photodetector receiving the fifth optical signal from the seventh waveguide, the seventh waveguide, the fourth open cell, the fourth microring resonator, and the fourth photodetector defining a second test branch; and a second comparator in communication with the third and fourth photodetectors for comparing wavelengths of the optical signals in the second reference branch and the second test branch and calculating a second wavelength shift therebetween, the detector confirming presence of the analyte in the second test sample when the second wavelength shift is substantially non-zero.

8. The optical analyte detector as recited in claim 7, wherein the fourth, fifth, sixth and seventh waveguides each comprise silicon or silicon carbide.

9. The optical analyte detector as recited in claim 8, wherein each of the third and fourth transition metal dichalcogenide monolayers comprises a transition metal dichalcogenide selected from the group consisting of $MoS_2$, $MoSe_2$, $WS_2$, and $WSe_2$.

10. The optical analyte detector as recited in claim 7, wherein each of the third and fourth transition metal dichalcogenide monolayers is functionalized with an adsorbed layer for detection of a particular analyte.

11. The optical analyte detector according to claim 1, wherein said light source comprises a III-V vertical-cavity surface-emitting laser (VCSEL).

12. The optical analyte detector according to claim 1, wherein said photodetectors comprise photodiodes.

13. A method for detecting COVID-19 infection using a silicon photonic biosensor device, comprising the steps of:

directing an optical signal through a waveguide formed on a silicon photonic biosensor device;

splitting the optical signal with a 1:1 power splitter into a reference optical signal propagating through a reference waveguide formed on the device and a test optical signal propagating through a test waveguide formed on the device;

placing a volume of a reference solution containing at least one antibody selectively binding to SARS-COV-2 virus in a reference cavity formed in a surface of the device above a reference microring resonator optically coupled to the reference waveguide, the device having a monolayer of a transition metal dichalcogenide disposed between the reference cavity and the reference microring resonator;

placing a volume of a test solution containing the antibody selectively binding to SARS CoV-2 virus in a test cavity formed in the surface of the device above a test microring resonator optically coupled to the test waveguide, the device having a monolayer of a transition metal dichalcogenide disposed between the test cavity and the test microring resonator;

obtaining a sample of nasopharyngeal fluid from a subject being tested for COVID-19 infection on a swab;

suspending the swab in the test cavity formed in the surface of the silicon photonic biosensor device;

detecting the reference optical signal in the reference waveguide downstream from the reference cavity;

measuring the wavelength of the detected reference optical signal;

detecting the test optical signal in the test waveguide downstream from the test cavity;

measuring the wavelength of the detected test optical signal;

comparing the measured wavelength of the reference optical signal with the measured wavelength of the test optical signal to define any difference between the wavelengths;

diagnosing the subject as being infected with the COVID-19 infection when the difference between the wavelengths is greater than 0.01 nm; and diagnosing the subject as being free of the COVID-19 infection when the difference between the wavelengths is less than 0.01 nm.

14. The method for detecting COVID-19 infection according to claim 13, wherein the at least one antibody selectively binding to SARS-CoV-2 virus comprises at least one antibody selectively binding to the SARS-CoV-2 spike protein.

15. The method for detecting COVID-19 infection according to claim 13, further comprising the steps of:

comparing the greater than 0.01 nm difference between the wavelengths to a reference chart plotting the difference between the wavelengths against number of days since exposure to the SARS-CoV-2 virus as determined by polymerase chain reaction (PCR); and diagnosing the subject as being exposed to SARS-CoV-2 virus by the corresponding number of days shown on the reference chart.

16. The method for detecting COVID-19 infection according to claim 13, further comprising the steps of:

comparing the greater than 0.01 nm difference between the wavelengths to a reference chart plotting the difference between the wavelengths against concentration of the SARS-CoV-2 virus as determined by polymerase chain reaction (PCR); and diagnosing the subject as having a concentration of the SARS-CoV-2 virus by the corresponding concentration shown on the reference chart.

* * * * *